United States Patent [19]

Steinmetz et al.

[11] Patent Number: 4,847,406

[45] Date of Patent: Jul. 11, 1989

[54] PROCESS FOR THE CO-PRODUCTION OF AROMATIC CARBOXYLATES AND ALKYL IODIDES

[75] Inventors: Guy R. Steinmetz; Mark Rule, both of Kingsport, Tenn.

[73] Assignee: Eastman Kodak Company, Rochester, N.Y.

[21] Appl. No.: 2,522

[22] Filed: Jan. 12, 1987

[51] Int. Cl.[4] .................. C07C 67/36; C07C 17/24
[52] U.S. Cl. ............................. 560/80; 560/76; 560/97; 560/100; 560/102; 560/103; 560/112; 570/181; 570/261
[58] Field of Search ............... 560/76, 80, 97, 100, 560/102, 103, 112; 570/181, 261

[56] References Cited

U.S. PATENT DOCUMENTS

| | | | |
|---|---|---|---|
| 2,565,462 | 8/1951 | Prichard et al. | 560/97 |
| 2,565,464 | 8/1951 | Tabet | 560/97 |
| 2,640,071 | 5/1953 | Leibu | 560/97 |
| 3,988,358 | 10/1976 | Heck | 560/97 X |
| 4,374,262 | 2/1983 | McGinnis et al. | 560/56 |

Primary Examiner—Werren B. Lone
Assistant Examiner—Vera C. Clarke
Attorney, Agent, or Firm—Charles R. Martin; William P. Heath, Jr.

[57] ABSTRACT

Disclosed is a process for the co-production of aromatic carboxylates and alkyl iodides by the carbonylation of aromatic iodides in the presence of an alkanol and a ruthenium catalyst.

11 Claims, No Drawings

PROCESS FOR THE CO-PRODUCTION OF AROMATIC CARBOXYLATES AND ALKYL IODIDES

DESCRIPTION

This invention relates to a novel carbonylation process for the preparation of both aromatic carboxylic acids or esters and an iodine containing compound from which the iodine values can be economically recovered. The carbonylation is conducted in the presence of an alkanol and a catalytic amount of ruthenium.

The carbonylation of aromatic halides in the presence of various Group VIII metal catalysts to obtain aromatic carboxylic acids and esters is well known in the art. For example, U.S. Pat. No. 3,988,358 discloses the palladium-catalyzed carbonylation of aromatic halides in the presence of an alcohol and a tertiary amine to produce the corresponding carboxylic acid ester. Nakayama and Mizoroki (Bull. Chem. Soc. Japan 42, 1124 (1969)) disclose the nickel-catalyzed carbonylation of aromatic halides in the presence of an alcohol and potassium acetate to produce the corresponding acid ester.

While it is known that aromatic iodides can be carbonylated the use of these materials has been discouraged by the cost associated with the difficulty of recovery the iodine values. For example, the use of basic materials in the carbonylation of aromatic halides, such as tri n-butyl amine in U.S. Pat. No. 3,988,358, results in the formation of halide salts from which the halide values can be reclaimed only through uneconomical procedures involving severe chemical treatments.

We have discovered a process which not only results in the carbonylation of aromatic iodides to aromatic carboxylic acids or esters in excellent yields and at excellent rates of conversion but also a process which results in production of alkyl iodides from which the iodine values can be economically recovered. In this invention the carbonylation is conducted in the presence of an alkanol and a catalytic amount of a ruthenium catalyst under aromatic carboxylic ester and alkyl iodide-forming conditions of temperature and pressure. The advantage afforded by our invention over the prior art is two-fold. First, the ruthenium-based catalyst has not been disclosed or recognized in the prior art to be an efficient carbonylation catalyst for aryl halides. Second, the iodine values in the alkyl iodide may be readily recovered by simply flashing the relatively volatile alkyl iodide from the mixture resulting from the carbonylation reaction. This can be accomplished either in the carbonylation reactor or, more preferably, in a pressure reduction vessel to which the mixture resulting from the carbonylation reaction is fed.

The ratio of aromatic acids to esters produced in the present invention is dependent on the ratio of alkanol to water present in the carbonylation reactor and on the choice or organic co-solvent. In general, minimizing the ratio of alkanol to water maximizes the production of acid. Conversely maximizing the ratio of alkanol to water maximizes the production of ester.

The aromatic iodides which may be used in our process may be monoiodo or polyiodo, e.g. di-, tri-and tetra-iodo aromatic compounds. The aromatic nucleus or moiety can contain from 6 to 18 carbon atoms, preferably 6 to 10 carbon atoms and may be carbocyclic aromatic such as benzene, biphenyl, terphenyl, napthalene, anthracene, etc., or heterocyclic aromatic such as pyridine, thiophene, pyrrole, indole, etc. In addition to one or more iodine atoms, the aromatic moiety may be substituted by various substituents inert under the conditions employed in our process. Examples of such substituents include alkyl of up to about 12 carbon atoms such as methyl, ethyl, isobutyl, hexyl, 2-ethylhexyl, nonyl, decyl, dodecyl, etc.; cycloalkyl of about 5 to 12 carbon atoms such as cyclopentyl, cyclohexyl, 4-butylcyclohexyl, etc.; hydroxy; alkoxy of up to about 12 carbon atoms such as methoxy, ethoxy, propoxy, butoxy, octyloxy, etc.; halogen such as chloro and bromo; alkoxycarbonyl of from 2 to about 8 carbon atoms such as methoxycarbonyl, ethoxycarbonyl, butoxycarbonyl, hexyloxycarbonyl, etc.; carboxyl; cyano; alkenyl of about 2 to 12 carbon atoms such as vinyl, allyl, etc.; formyl; alkanoyl of about 2 to 8 carbon atoms such as acetyl, propionyl, butyryl, hexanoyl, etc.; alkanoylamido of about 2 to 8 carbon atoms such as acetamido, butylamido, etc.; aroylamino such as benzamido; and alkylsulfonamide such as methanesulfonamide, hexanesulfonamido, etc.

Specific examples of the aromatic iodide reactants include iodobenzene 1,3- and 1,4-diiodobenzene, 1,3,5-triiodobenzene, 4-iodotoluene, 4-iodophenol, 4-iodoanisole, 4-iodoacetophenone, 4,4'-diiodobiphenyl, 4-chloroiodobenzene, 3-bromoiodo-benzene, and 2,6- and 2,7-diiodonaphthalene. Our process is particularly useful for the preparation of benzenedicarboxylic and naphthalenedicarboxylic acids and their esters and thus the preferred reactants are diiodobenzenes, especially 1,3- and 1,4-diiodobenzene, and diiodonaphthalenes, especially 2,6- and 2,7-diiodonapththalene.

The aromatic iodide reactants are known compounds and/or can be prepared according to published procedures. For example, T. Hudlicky et al *The Chemistry of Halides, Pseudohalides and Azides*, Supplement D, Part 2, 1142-1158, the disclosure of which is incorporated herein by reference in its entirety, discloses a number of such processes. Another process described in J. Chem. Soc. 150 (1952) comprises treating an aromatic compound, such as benzene, with iodine in the presence of silver sulfate dissolved in concentrated sulfuric acid.

The alkanol used in the process of this invention normally is methanol sine it is the least expensive, results in the formation of methyl carboxylate esters, which may be used in transesterification reactions, and produces methyl iodide which is the most volatile of the alkyl iodides. However, other alkanols, for example, alkanols containing up to about 12 carbon atoms, preferably up to about 4 carbon atoms, may be employed if desired. Examples of such alkanols include ethanol, propanol, butanol, pentanol, hexanol, heptanol, octanol, decanol, ethylene glycol, diethylene glycol, benzyl alcohol, and the like. If aromatic esters are desired, about two moles of alkanol are required for each mole equivalent of iodoaromatic reacting. For each mole equivalent of aromatic acid produced, one mole of alkanol is required.

The process provided by our invention can also be carried out in the presence of an organic co-solvent such as aliphatic, alicyclic and aromatic hydrocarbons, halogenated hydrocarbons and ethers. Examples of such solvents include benzene, toluene, the xylenes, hexane, heptane, chlorobenzene, ethylene dicholoride, methylchloroform, diethyl ether, methyl t-butyl ether, diglyme, acetic acid, benzoic acid, methyl benzoate, etc. However, the use of a co-solvent is not critical to the practice of this invention.

The ruthenium catalyst can be provided to the reaction medium as any of a number of ruthenium salts or complexes that are capable of providing ruthenium in a soluble form in the reaction. Illustrative sources of ruthenium are ruthenium trichloride, ruthenium tribromide, ruthenium triiodide, ruthenium acetate, ruthenium acetylacetonate, ruthenium dioxide, ruthenium tetraoxide, ruthenium pentacarbonyl and dodecacarbonyltriruthenium and their phosphine and halogen substituted analogs. The amount of ruthenium is not significant as long as enough is present to catalyze the reaction. Preferably, the catalyst is present in a concentration of 10 to 0.01 mole percent, preferably 1.0 to 0.1 mole percent, based on the moles of aromatic iodide reactant. Therefore, the total reaction medium has a catalyst concentration of about 10,000 ppm to 10 ppm with preferred catalyst concentrations of 1000 to 100 ppm.

The carbonylation reaction is conducted in the presence of carbon monoxide, which is employed in amounts such that the total reaction pressure is suitable for the formation of both the aromatic carboxylic ester and the alkyl iodide. The carbon monoxide employed may be essentially pure or it may contain other gases such as carbon dioxide, hydrogen, methane and other compounds produced by synthesis gas plants. Normally, th carbon monoxide will be at least 90, preferably at least 95, percent pure.

The process of the present invention can be conducted at temperatures and pressures suitable for formation of both the aromatic carboxylic acid and alkyl iodide. The temperatures and pressures are interdependent and can vary considerably. While the process can be carried out at pressures as high as 10,000 psig, the cost of utilities and equipment required for such high pressure operation cannot normally be commercially justified. Thus, the pressure normally will be in the range of about 300 to 4000 psig, preferably about 750 to 1500 psig. A particularly preferred pressure is 1000 psig. While temperatures as low as 125° C. and higher than 225° C. may be used, our process normally is carried out between about 125° to 225° C. The preferred temperature range is 150° to 200° C. A particularly preferred temperature is 175° C.

The relative amounts of carbon monoxide, alkanol and aromatic iodide used in our process can be varied substantially and are, in general, not critical as long as there is at least a stoichiometric amount present.

When a polyiodo aromatic compound is used as the reactant in our carbonylation process, the products obtained include both aromatic polycarboxylic esters and partially carbonylated products such as iodo aromatic carboxylic esters. The latter compounds are useful as intermediates in the preparation of derivatives of aromatic carboxylic esters, for example, by displacement reactions whereby the iodo substituent is replaced with other radicals. The difunctional esters, such as dimethyl 2,6-naphthalene dicarboxylate, can be reacted with diols to produce high molecular weight polyesters suitable for molding plastics. Useful articles can be molded from these plastics, such as by injection molding. The relative amounts of partially or totally carbonylated products is highly dependent on the period of time that the reactant resides under carbonylation conditions. For example, the carbonylation of diiodobenzene at 175° C. and 750 psig in accordance with our invention over varying periods of time results in varying amounts of reactant, iodo ester and diester.

The alkyl iodides prepared according to the process of our invention may be used in other chemical processes such as in the preparation of carboxylic acids and carboxylic anhydrides according to known carbonylation procedures. Alternatively, the alkyl iodide can be oxidatively decomposed at elevated temperature to produce a gaseous mixture of iodine, carbon dioxide and water from which the iodine can be recovered. Alternatively, the alkyl iodides may be thermally decomposed to iodine and an alkane.

Our process is carried out at a pKa of less than 5. Therefore, there are no significant amounts of basic materials which preferentially combine with hydrogen iodide and interfere with the formation of an alkyl iodide. Examples of such bases which are not present in significant amounts in our process include amines, particularly tertiary amines, and hydroxides, alkoxides and weak acid salts, e.g. carboxylates, of the alkali and alkaline earth metals.

Our process is particularly useful for the preparation of dialkyl esters of aromatic dicarboxylic acids such as 1,3- and 1,4-benzene-dicarboxylic and 2,6- and 2,7-naphthalene-dicarboxylic acid esters. Such diesters may be used in the preparation of polyesters such as poly-(ethylene terephthalate) and poly(ethylene 2,6-naphthalenedicarboxylate).

The process of this invention can be carried out as a batch, semi-continuous or continuous operation. In the manufacture of dialkyl esters of aromatic dicarboxylic acids in the quantities required for use in the preparation of polyesters such as those mentioned above, the process described hereinabove will be carried out in a continuous manner. A typical continuous method of practicing our process comprises feeding into a mixed pressure vessel a liquid stream of methanol, another liquid stream composed of 2,6-diiodonaphthalene, optionally an organic solvent and the ruthenium catalyst and a gaseous stream of carbon monoxide. The pressure vessel is equipped with a means for maintaining the desired temperature and pressure. The liquid mixture from the reactor is passed to a flash column where the methyl iodide and inert organic solvent is flashed off. The flashed vapor stream is then condensed and the methyl iodide and methanol separated by decanting. The liquid from the flash column is centrifuged and 2,6-naphthalene dicarboxylic acid is separated from the solution containing the ester of 2,6-naphthalene dicarboxylic acid. The desired 2,6-naphthalene dicarboxylic ester is then recovered by selective recrystallization and the remaining mixture containing unreacted iodoaromatics and ruthenium catalyst is recycled.

Our invention is further illustrated by the following examples. In the procedures utilized in the examples the materials employed are loaded into a 330 ml autoclave constructed of Hastelloy B2 alloy which is designed to operate in a rocking mode. The autoclave is pressurized with 500 psig carbon monoxide gas pressure at room temperature and then the gas is vented and the autoclave is sealed. In these examples the autoclave is pressurized to 250 psig with carbon monoxide gas at ambient temperature and heated and rocked until reaction temperature was reached, at which time additional carbon monoxide gas is added to increase the autoclave internal pressure to the predetermined value. Reactor pressure is maintained by adding carbon monoxide at the same rate at which it is consumed by the reactants. The carbon monoxide used is essentially pure. When the predetermined reaction time is completed the autoclave is cooled by a stream of cold air to approximately 25° C. After the gas is vented from the autoclave the crude product is analyzed by gas chromatographic methods. The % conversion is the mole percent of iodo-group converted to carboxylic acid or ester. The ester/acid ratio is the mole ratio of total ester and acid groups formed. The grams of alkyl iodide found were determined by gas chromatographic analysis of the reaction solution. The results of these runs are shown below.

| Example No. | | |
| --- | --- | --- |
| | 1 | 2 |
| Iodoaromatic | p-diiodobenzene | p-diiodobenzene |
| wt (g) | 20 | 20 |
| Alkanol | methanol | methanol |
| wt (g) | 24 | 24 |
| Co-Solvent | toluene | toluene |
| wt (g) | 56 | 56 |
| Catalyst | RuCl$_3$.3H$_2$O | RuCl$_3$.3H$_2$O |
| wt (g) | 0.50 | 0.10 |
| Time (Hr) | 3 | 3 |
| Pressure (psig) | 1000 | 750 |
| Temp (°C.) | 175 | 175 |
| % Conversion | 100 | 45 |
| Ester/Acid | 4.3 | 24.6 |
| g. Alkyl Iodide | 16 | 7 |
| | 3 | 4 |
| Iodoaromatic | iodobenzene | iodobenzene |
| wt (g) | 60 | 61 |
| Alkanol | methanol | methanol |
| wt (g) | 39 | 39 |
| Co-Solvent | toluene | toluene |
| wt (g) | 82 | 82 |
| Catalyst | RuCl$_3$.3H$_2$O | RuCl$_3$.3H$_2$O |
| wt (g) | 0.50 | 0.50 |
| Time (Hr) | 4 | 4 |
| Pressure (psig) | 1500 | 4000 |
| Temp (°C.) | 175 | 175 |
| % Conversion | 39 | 100 |
| Ester/Acid | 7.5 | 6.5 |
| g. Alkyl Iodide | 15 | 40 |
| | 5 | 6 |
| Iodoaromatic | p-iodophenol | 2,6/2,7-diiodonaphthalene |
| wt (g) | 15 | 25 |
| Alkanol | methanol | methanol |
| wt (g) | 39 | 39 |
| Co-Solvent | toluene | toluene |
| wt (g) | 82 | 82 |
| Catalyst | RuCl$_3$.3H$_2$O | RuCl$_3$.3H$_2$O |
| wt (g) | 0.50 | 0.50 |
| Time (Hr) | 4 | 4 |
| Pressure (psig) | 1500 | 1500 |
| Temp (°C.) | 175 | 175 |
| % Conversion | 100 | 94 |
| Ester/Acid | 10.2 | 6.6 |
| g. Alkyl Iodide | 9 | 16 |
| | 7 | 8 |
| Iodoaromatic | iodobenzene | iodobenzene |
| wt (g) | 60 | 60 |
| Alkanol | methanol | ethanol |
| wt (g) | 40 | 39 |
| Co-Solvent | acetic acid | toluene |
| wt (g) | 99 | 82 |
| Catalyst | RuCl$_3$.3H$_2$O | RuCl$_3$.3H$_2$O |
| wt (g) | 0.50 | 0.50 |
| Time (Hr) | 4 | 4 |
| Pressure (psig) | 1500 | 1500 |
| Temp (°C.) | 175 | 175 |
| % Conversion | 75 | 45 |
| Ester/Acid | 0.42 | 5.5 |
| g. Alkyl Iodide | 30 | 18 |

While the invention has been described in detail with particular reference to preferred embodiments thereof, it will be understood that variations and modifications an be effected within the spirit and scope of the invention.

We claim:

1. A process comprising:
   (A) co-production of an aromatic carboxylic ester and an alkyl iodide by carbonylating an aromatic iodide in the presence of carbon monoxide an alkanol and a catalytic amount of a ruthenium catalyst under aromatic carboxylic ester and alkyl iodide-forming conditions of temperatures and pressure wherein there are no significant amounts of basic materials which preferentially combine with hydrogen iodide and interfere with the formation of an alkyl iodide, and
   (B) recovering the alkyl iodide.

2. The process of claim 1 wherein the aromatic iodide is selected from the group consisting of diiodonaphthalene and diiodobenzene.

3. The process of claim 2 wherein the diiodonaphthalene is 2,6-diiodonaphthalene and the diiodobenzene is 1,4-diiodobenzene.

4. The process of claim 1 wherein the alkanol is methanol.

5. The process of claim 1 wherein the temperature is in the range of about 125° to 225° C.

6. The process of claim 5 wherein the temperature is in the range of about 150°–200° C.

7. The process of claim 1 wherein the pressure is in the range of 300 to 4000 psig.

8. The process of claim 7 wherein the pressure is in the range of 750 to 1,500 psig.

9. The process of claim 1 wherein the process is carried out in the presence of an organic co-solvent.

10. A process comprising
    (A) co-production of an aromatic dicarboxylate selected from the group consisting of a benzenedicarboxylate and a naphthalene dicarboxylate and methyl iodide by carbonylating a diiodobenzene or a diiodonaphthalene in the presence of carbon monoxide methanol, an organic solvent and a catalytic amount of a ruthenium catalyst at a temperature of about 150° to 200° C. and a pressure of about 750 to 1,500 psig wherein there are no significant amounts of basic materials which preferentially combine with hydrogen iodide and interfere with the formation of an alkyl iodide, and
    (B) recovering the methyl iodide.

11. A process comprising
    (A) co-production of dimethyl 2,6-naphthalenedicarboxylate and methyl iodide by carbonylating 2,6-diiodonaphthalene in the presence of carbon monoxide, methanol, an organic co-solvent and a catalytic amount of ruthenium at a temperature of about 175° C. and a pressure of about 1,000 psig wherein there are no significant amounts of basic materials which preferentially combine with hydrogen iodide and interfere with the formation of an alkyl iodide, and
    (B) recovering the methyl iodide.

* * * * *